(12) United States Patent
Strohl

(10) Patent No.: US 7,700,099 B2
(45) Date of Patent: Apr. 20, 2010

(54) NON-IMMUNOSTIMULATORY ANTIBODY AND COMPOSITIONS CONTAINING THE SAME

(75) Inventor: William R. Strohl, Bridgewater, NJ (US)

(73) Assignee: Merck & Co., Inc., Rahway, NJ (US)

( * ) Notice: Subject to any disclaimer, the term of this patent is extended or adjusted under 35 U.S.C. 154(b) by 601 days.

(21) Appl. No.: 11/581,931

(22) Filed: Oct. 17, 2006

(65) Prior Publication Data

US 2007/0148167 A1 Jun. 28, 2007

Related U.S. Application Data

(63) Continuation-in-part of application No. 11/256,332, filed on Oct. 21, 2005.

(60) Provisional application No. 60/652,538, filed on Feb. 14, 2005.

(51) Int. Cl.
- A61K 39/00 (2006.01)
- A61K 39/395 (2006.01)
- C07K 16/00 (2006.01)

(52) U.S. Cl. .............. 424/133.1; 424/130.1; 530/387.1; 435/810

(58) Field of Classification Search ........................ None
See application file for complete search history.

(56) References Cited

U.S. PATENT DOCUMENTS

| | | | |
|---|---|---|---|
| 5,624,821 A | 4/1997 | Winter et al. ............... | 435/69.6 |
| 5,648,260 A | 7/1997 | Winter et al. ............ | 435/252.3 |
| 6,737,056 B1 | 5/2004 | Presta ..................... | 424/133.1 |
| 7,361,740 B2 * | 4/2008 | Hinton et al. ............ | 530/387.3 |

FOREIGN PATENT DOCUMENTS

| WO | WO 94/29351 | 12/1994 |
|---|---|---|
| WO | WO 97/11971 | 4/1997 |
| WO | WO 99/58572 | 11/1999 |

OTHER PUBLICATIONS

Wells, 1990, Biochemistry 29:8509-8517.*
Ngo et al., 1994, The Protein Folding Problem and Tertiary Structure Prediction, pp. 492-495.*
Bork, 2000, Genome Research 10:398-400.*
Skolnick et al., 2000, Trends in Biotech. 18(1):34-39.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Ellison et al DNA 1: 11-18, 1981.*
Alyanakian et al., "Pharmacokinetics of total immunoglobulin G and immunoglobulin G subclasses in patients undergoing replacement therapy for primary immunodeficiency syndromes", Vox Sanguinis 2003 84:188-192.
Burton et al., "The Clq receptor site on immunoglobulin G", Nature 1980 288:338-344.
Brekke et al., "Human IgG isotype-specific amino acid residues affecting complement-mediated cell lysis and phagocytosis", Eur. J. Immunol. 1994 24:2542-2547.
Burton et al., "Immunoglobulin G:Functional Sites", Molecular Immunology 1985 22(3):161-206.
Chappel et al., "Identification of the $Fc_\gamma$ receptor class I binding site in human IgG through the use of recombinant IgG1/IgG2 hybrid and point-mutated antibodies", Proc. Natl. Acad. Sci. USA 1991 88:9036-9040.
Cooper et al., "The classical complement pathway:activation and regulation of the first complement component", Advances in Immunology 1985 37:151-216.
Daëron, Marc, "Fc receptor biology", Annu. Rev. Immunol. 1997 15:203-234.
Haas et al.,"$Fc_\gamma$ receptors of phagocytes", J Lab Clin Med 1995 126:330-341.
Deisenhofer, Johann, "Crystallographic refinement and atomic modelsof a human Fc fragment and its complex with fragment B of protein A from *Staphylococcus aureus* at 2.9-2.8-Å resolution", Biochemistry 1981 20(9):2361-2370.
Duncan et al., "The binding site for Clq on IgG", Nature 1988 332:738-740.
Duncan et al., "Localization of the binding site for the human high-affinity Fc receptor on IgG", Nature 1988 332:563-564.
Ghetie et al., "Multiple roles for the major histocompatibility complex class I-related receptor FcRn", Annu. Rev. Immunol. 2000 18:739-766.
Greenwood et al., "Structural motifs involved in human IgG antibody effector functions", Eur. J. Immunol. 1993 23:1098-1104.
Guyer et al., "Immunoglobulin binding by mouse intestinal epithelial cell receptors", The Journal of Immunology 1976 117(2):587-593.
Idusogie et al., "Mapping of the Clq binding site on rituxan, a chimeric antibody with a human IgG1 Fc", The Journal of Immunology 2000 164:4178-4184.
Kim et al., "Analysis of FcγRIII and IgG Fc polymorphism reveals functional and evolutionary implications of protein-protein interaction", J Mol Evol 2001 53:1-9.
Lund et al., "Multiple binding sites on the $C_H2$ domain of IgG for mouse FcγRII", Molecular Immunology 1992 29(1):53-59.
Medgyesi et al., "Functional mapping of the FcγRII binding site on human IgG1 by snthetic peptides", Eur. J. Immunol. 2004 34:1127-1135.

(Continued)

*Primary Examiner*—Jeffrey Stucker
*Assistant Examiner*—Aditi Dutt
(74) *Attorney, Agent, or Firm*—Licata & Tyrrell P.C.

(57) ABSTRACT

The present invention relates to a non-immunostimulatory antibody which lacks antibody-dependent cell-mediated cytotoxicity, Fc gamma receptor binding and complement-mediated cytotoxicity. In some embodiments, the antibody contains a modified immunoglobulin G2 (IgG2) Fc region with at least one substitution in the B/C loop, FcRn binding domain, and the F/G loop. The antibody of the invention is useful in the preparation of therapeutic antibodies and pharmaceutical compositions and kits containing the same.

4 Claims, 3 Drawing Sheets

OTHER PUBLICATIONS

Ravetch et al., "Fc receptors", Annu. Rev. Immunol. 1991 9:457-492.

Sarmay et al., "Ligand inhibition studies on the role of Fc receptors in antibody-dependent cell-mediated cytotoxicity", Molecular Immunology 1984 21(1):43-51.

Shields et al., "High resolution mapping of the binding site on human IgG1 for FcγRI, FcγRII, FcγRIII, and FcRn and design of IgG1 variants with improved binding to the FcγR", J Biol Chem 2001 276(9):6591-6604.

Thommesen et al., "Lysine 322 in the human IgG3 $C_H2$ domain is crucial for antibody dependent complement activation", Molecular Immunology 2000 37:995-1004.

Ward et al., "The effector functions of immunoglobulins: implications for therapy", Therapeutic Immunology 1995 2:77-94.

Woof et al., "Localisation of the monocyte-binding region on human immunoglobulin G", Molecular Immunology 1986 23(3):319-330.

Zuckier et al., "The use of severe combined immunodeficiency mice to study the metabolism of human immunoglobulin G", Cancer 1994 73:794-799.

Kabat et al., "Sequences of proteins of immunological interest", 5th Edition Public Health Service, National Institutes of Health, Betheseda, MD, 1991.

Armour et al., "Recombinant human IgG molecules lacking Fcγ receptor I binding and monocyte triggering activities", Eur. J. Immunol. 1999 29:2613-2624.

Canfield et al., "The binding affinity of human IgG for its high affinity Fc receptor is determined by multiple amino acids in the CH2 domain and is modulated by the hinge region", J. Exp. Med. 1991 173:1483-1491.

Hougs et al., "The first constant-domain (CH1) exon of human IGHG2 is polymorphic and in strong linkage disequilibrium with the CH2 exon polymorphism encoding the G2m(n+) allotype in caucasians", Immunogenetics 52:242-248, 2001.

Gergely et al., "Fc receptors on lymphocytes and K cells", 607th Meeting, London 1984 12:739-743.

\* cited by examiner

```
              |--- CH1 STARTS HERE          C144
IgG1    /// ASTK GPSVFPLAPS SKSTSGGTAA LGCLVKDYFP EPVTVSWNSG
IgG2    /// ASTK GPSVFPLAPC SRSTSESTAA LGCLVKDYFP EPVTVSWNSG
IgG4    /// ASTK GPSVFPLAPC SRSTSESTAA LGCLVKDYFP EPVTVSWNSG
IgG2M4  /// ASTK GPSVFPLAPC SRSTSESTAA LGCLVKDYFP EPVTVSWNSG
        (VH-C1 LINKER)
                                                      C200
IgG1    ALTSGVHTFP AVLQSSGLYS LSSVVTVPSS SLGTQTYICN VNHKPSNTKV
IgG2    ALTSGVHTFP AVLQSSGLYS LSSVVTVTSS NFGTQTYTCN VDHKPSNTKV
IgG4    ALTSGVHTFP AVLQSSGLYS LSSVVTVPSS SLGTKTYTCN VDHKPSNTKV
IgG2M4  ALTSGVHTFP AVLQSSGLYS LSSVVTVTSS NFGTQTYTCN VDHKPSNTKV

-HINGE REGION--||----CH2-> P238         M252    C261
IgG1    DKKAEPKSCD KTHTCPPCPA PELLGGPSVF LFPPKPKDTL MISRTPEVTC
IgG2    DKTVERKCC- --VECPPCPA PP-VAGPSVF LFPPKPKDTL MISRTPEVTC
IgG4    DKRVESKYGP ---PCPSCPA PEFLGGPSVF LFPPKPKDTL MISRTPEVTC
IgG2M4  DKTVERKCC- --VECPPCPA PP-VAGPSVF LFPPKPKDTL MISRTPEVTC
                           (LOWER HINGE)         FcRn-BIND

Q268                           N297*      L309
IgG1    VVVDVSHEDP EVKFNWYVDG VEVHNAKTKP REEQYNSTYR VVSVLTVLHQ
IgG2    VVVDVSHEDP EVQFNWYVDG VEVHNAKTKP REEQFNSTFR VVSVLTVVHQ
IgG4    VVVDVSQEDP EVQFNWYVDG VEVHNAKTKP REEQFNSTYR VVSVLTVLHQ
IgG2M4  VVVDVSQEDP EVQFNWYVDG VEVHNAKTKP REEQFNSTFR VVSVLTVLHQ
        B/C LOOP                        C'E LOOP    FcRn-BIND
                          P331
            C321          A330   |----CH3->
IgG1    DWLNGKEYKC KVSNKALPAPI EKTISKAKG QPREPQVYTL PPSRDELTKN
IgG2    DWLNGKEYKC KVSNKGLPAPI EKTISKTKG QPREPQVYTL PPSREEMTKN
IgG4    DWLNGKEYKC KVSNKGLPSSI EKTISKAKG QPREPQVYTL PPSQEEMTKN
IgG2M4  DWLNGKEYKC KVSNKGLPSSI EKTISKTKG QPREPQVYTL PPSREEMTKN
                      F/G LOOP

IgG1    QVSLTCLVKG FYPSDIAVEW ESNGQPENNY KTTPPVLDSD GSFFLYSKLT
IgG2    QVSLTCLVKG FYPSDIAVEW ESNGQPENNY KTTPPMLDSD GSFFLYSKLT
IgG4    QVSLTCLVKG FYPSDIAVEW ESNGQPENNY KTTPPVLDSD GSFFLYSRLT
IgG2M4  QVSLTCLVKG FYPSDIAVEW ESNGQPENNY KTTPPMLDSD GSFFLYSKLT

M428L H433
IgG1    VDKSRWQQGN VFSCSVMHEA LHNHYTQKSL SLSPGK* (SEQ ID NO:2)
IgG2    VDKSRWQQGN VFSCSVMHEA LHNHYTQKSL SLSPGK* (SEQ ID NO:3)
IgG4    VDKSRWQEGN VFSCSVMHEA LHNHYTQKSL SLSLGK* (SEQ ID NO:4)
IgG2M4  VDKSRWQQGN VFSCSVMHEA LHNHYTQKSL SLSPGK* (SEQ ID NO:1)
                              FcRn-BIND
```

FIG. 1

NON-IMMUNOSTIMULATORY ANTIBODY AND COMPOSITIONS CONTAINING THE SAME

INTRODUCTION

This application is a continuation-in-part of U.S. patent application Ser. No. 11/256,332, filed Oct. 21, 2005, which is based on U.S. provisional application Ser. No. 60/652,538 filed Feb. 14, 2005, the contents of which is incorporated herein by reference in its entirety.

BACKGROUND OF THE INVENTION

Antibodies are proteins which exhibit binding specificity to a specific antigen. Native antibodies are usually heterotetrameric glycoproteins composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy and light chain has at one end a variable domain ($V_H$ and $V_L$) followed by a number of constant domains. The variable domains differ extensively in sequence among antibodies and are responsible for the binding specificity of each particular antibody for its particular antigen. However, the variability is not evenly distributed through the variable domains of antibodies. It is concentrated in three complementarity determining regions (CDRs) both in the light chain and the heavy chain variable domains. The CDRs in each chain are held together in close proximity by the framework regions and, with the CDRs from the other chain, contribute to the formation of the antigen binding site of antibodies (Kabat, et al. (1991) Sequences of Proteins of Immunological Interest, 5th Ed. Public Health Service, National Institutes of Health, Bethesda, Md).

The constant domains are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG and IgM, and in humans several of these are further divided into subclasses (isotypes), e.g., IgG1, IgG2, IgG3, and IgG4; IgA1 and IgA2. The human IgG isotypes, IgG1, IgG2, IgG3, and IgG4 elicit differential responses due to their sequence differences, which result in differential binding the to Fcγ receptors (Daeron (1997) *Annu. Rev. Immunol.* 15:203-234) and/or the initial complement component, C1q (Cooper (1985) *Adv. Immunol.* 37:151). Of the various human immunoglobulin classes, only human IgG1, IgG2, IgG3 and IgM are known to activate complement; and human IgG1 and IgG3 mediate ADCC more effectively than IgG2 and IgG4.

Papain digestion of antibodies produces two identical antigen binding fragments, called Fab fragments, each with a single antigen binding site, and a residual Fc fragment, whose name reflects its ability to crystallize readily. The crystal structure of the human IgG Fc region has been determined (Deisenhofer (1981) *Biochemistry* 20:2361-2370). In human IgG molecules, the Fc region is generated by papain cleavage N-terminal to Cys 226. The Fc region is central to the effector functions of antibodies.

The effector functions mediated by the antibody Fc region can be divided into two categories, namely effector functions that operate after the binding of antibody to an antigen (these functions involve the participation of the complement cascade or Fc receptor (FcR)-bearing cells); and effector functions that operate independently of antigen binding (these functions confer persistence in the circulation and the ability to be transferred across cellular barriers by transcytosis) (Ward and Ghetie (1995) *Therapeutic Immunology* 2:77-94).

The interaction of antibodies and antibody-antigen complexes with cells of the immune system effects a variety of responses, including antibody-dependent cell-mediated cytotoxicity (ADCC) and complement-mediated cytotoxicity (CMC) (see Daeron (1997) *Annu. Rev. Immunol.* 15:203-234; Ward and Ghetie (1995) supra; Ravetch and Kinet (1991) *Annu. Rev. Immunol.* 9:457-492).

Several antibody effector functions are mediated by Fc receptors (FcRs), which bind the Fc region of an antibody. FcRs are defined by their specificity for immunoglobulin isotypes; Fc receptors for IgG antibodies are referred to as FcγR, IgE for FcεR, etc. Three subclasses of FcγR have been identified, FcγRI (CD64), FcγRII (CD32) and FcγRIII (CD16). It is known, for example, that IgG1 and IgG3 isotypes bind FcγRI with a $K_d$ of approximately $10^9$ $M^{-1}$ (Canfield and Morrison (1991) *J. Exp. Med.* 173:1483-1491), but that the IgG4 isotype binds approximately 10-fold less affinity, and IgG2 isotype has an affinity for FcγRI more than 1000-fold greater (e.g., at least $10^6$ $M^1$; Canfield and Morrison (1991) supra). Another type of Fc receptor is the neonatal Fc receptor (FcRn). FcRn is structurally similar to major histocompatibility complex (MHC) and is composed of an α-chain noncovalently bound to β2-microglobulin. FcRn binds IgGs, internalizes them into endocytic vesicles, and then, through a pH-dependent step, recycles the antibodies back into the serum (Ghetie and Ward (2000) *Annu. Rev. Immunol.* 18:739-766). This process effectively increases the half-life of IgGs and gives them their nominal half-lives in serum of about 20 days (Ghetie and Ward (2000) supra).

C1q and two serine proteases, C1r and C1s, form the complex C1, the first component of the complement-dependent cytotoxicity (CDC) pathway. To activate the complement cascade, it is necessary for C1q to bind to at least two molecules of IgG1, IgG2, or IgG3, but only one molecule of IgM, attached to the antigenic target (Ward and Ghetie (1995) supra). Based upon the results of chemical modifications and crystallographic studies, the binding site for the complement subcomponent C1q on IgG has been suggested to involve the last two (C-terminal) β-strands of the CH2 domain (Burton, et al. (1980) *Nature* 288:338-344), with amino acid residues 318 to 337 involved in complement fixation (Burton, et al. (1985) *Mol. Immunol.* 22(3):161-206).

Key residues of the various IgG isotypes involved in binding to FcRs and C1q have been suggested. The binding site on human and murine antibodies for FcγR have been mapped to the lower hinge region composed of residues 233-239 (numbering as in Kabat, et al. (1991) supra; Woof, et al. (1986) *Mol. Immunol.* 23:319-330; Duncan, et al. (1988) *Nature* 332:563; Canfield and Morrison (1991) *J. Exp. Med.* 173: 1483-1491; Chappel, et al. (1991) *Proc. Natl. Acad. Sci USA* 88:9036-9040). Of residues 233-239, P238 and S239 have been cited as possibly being involved in binding. Other previously cited areas possibly involved in binding to FcγR include G316-K338 (human IgG) for human FcγRI (Woof, et al. (1986) supra); K274-R301 (human IgG1) for human FcγRIII (based on peptides) (Sarmay, et al. (1984) *Mol. Immunol.* 21:43-51); Y407-R416 (human IgG) for human FcγRIII (based on peptides) (Gergely, et al. (1984) *Biochem. Soc. Trans.* 12:739-743); as well as N297 and E318 (murine IgG2b) for murine FcγRII (Lund, et al. (1992) *Mol. Immunol.* 29:53-59). Peptide analysis of IgG1 demonstrates significant binding of residues 256-271 to FcγRIIb (Medgyesi, et al. (2004) *Eur. J. Immunol.* 34:1127-1135).

Armour, et al. ((1999) *Eur. J. Immunol.* 29:2613) further suggest the role of residues 230-236 in FcγRI binding. IgG2-like lower hinge regions and mutations at residues G327, S330, and S331 were inactive in binding FcγR as well as in complement-mediated cell lysis. Additional analysis of an IgG2 mutant with point mutations A230S and P231S, indicated reduced binding to the 131H polymorphism of FcγRIIa as compared to IgG2 and approximately equal binding to the 131R polymorphism of FcγRIIa as compared to IgG2. Moreover, this IgG2 mutant favored binding to the FcγRIIb inhibitory receptor. See also, WO 99/58572. A hybrid IgG2/IgG4 antibody, composed of IgG2 CH1 and hinge region fused to IgG4 at about residue P238, has also been disclosed which lacks binding to U937 cells which possess FcγRI (WO 97/11971).

Duncan and Winter (Nature 332:738-40 (1988)), using site-directed mutagenesis, reported that Glu318, Lys320 and Lys322 form the binding site for the murine C1q. The key role of these residues was further suggested by Thommesen, et al. ((2000) *Mol. Immunol.* 37:995-1004) and in U.S. Pat. Nos. 5,648,260 and 5,624,821. However, it was subsequently shown that these residues are not the same residues in human antibody binding to C1q. Alanine substitutions at positions D270A, K322A, P329A, and P331G of IgG1 have also been demonstrated to significantly reduce C1q binding and complement activation (Idusogie, et al. (2000) *J. Immunol.* 164:4178-4184).

Residue Pro331 has been implicated in C1q binding by analysis of the ability of human IgG subclasses to carry out complement-mediated cell lysis. Domain swapping between IgG2 and IgG3, as well as IgG1 and IgG4 has been used to dissect the function of residues 292-340, with mutations A330S and P331S eliminating C1q binding and mutation P331S reducing binding to FcγRI (Tao, et al. (1991) *J. Exp. Med.* 173:1025-1028; Canfield and Morrison (1991) supra; Greenwood, et al. (1993) *Eur. J. Immunol.* 23:1098-1104). The significance of A330 and P331 was also disclosed by Shields, et al. ((2001) *J. Biol. Chem.* 276:6591-6604) and in U.S. Pat. No. 6,737,056 and U.S. patent application Ser. No. 11/194,989. Site-directed mutation of P331S in IgG1 (Xu, et al. (1994) *J. Biol. Chem.* 269:3469-3474) and S331P in IgG4 (Brekke, et al. (1994) *Eur. J. Immunol.* 24:2542-2547) further suggested the key role of this residue in C1q binding and complement activation. Other reports suggest that human IgG1 residues Leu235, and Gly237, located in the lower hinge region, play a critical role in complement fixation and activation (Xu, et al. (1993) *J. Immunol.* 150:152A). Amino acid residues 231 to 238 have also been suggested to be necessary for C1q and FcR binding of human IgG1 (WO 94/29351).

Therapeutic antibodies for the treatment of a variety of diseases are known in the art. It is desirable that these antibodies do not provoke an immune reaction toward cells harboring the target antigen. Therefore, there is a need in the art for the generation of therapeutic human or humanized monoclonal antibodies that do not possess any effector functionality, yet retain the typical pharmacookinetics of an IgG. The present invention meets this need in the art.

SUMMARY OF THE INVENTION

The present invention is an isolated non-immunostimulatory antibody, wherein said antibody lacks antibody-dependent cell-mediated cytotoxicity, Fc gamma receptor binding and complement-mediated cytotoxicity. In some embodiments, the antibody retains a substantial portion of an immunoglobulin G2 (IgG2) Fc region. In other embodiments, the IgG2 Fc region contains at least one substitution in the B/C loop, FcRn binding domain, and the F/G loop. In still other embodiments, substitutions in the IgG2 Fc region are at amino acid residues 268, 309, 330 and 331 according to the Kabat numbering system. In particular embodiments, the present invention embraces a non-immunostimulatory antibody having an amino acid sequence set forth in SEQ ID NO:1. A pharmaceutical composition and kit containing the isolated non-immunostimulatory antibody of the invention are also provided as is a method for preventing binding of an antibody to an Fc receptor or complement.

BRIEF DESCRIPTION OF THE DRAWINGS

FIG. 1 shows a comparison of the amino acid sequence of human antibody constant regions and the sequence of IgG2m4. The asterisk indicates a glycosylation site at Asn297. Regions of FcRn binding are indicated. Sequences in which IgG2m4 is different from IgG2 are underlined.

DETAILED DESCRIPTION OF THE INVENTION

Figure 2A:
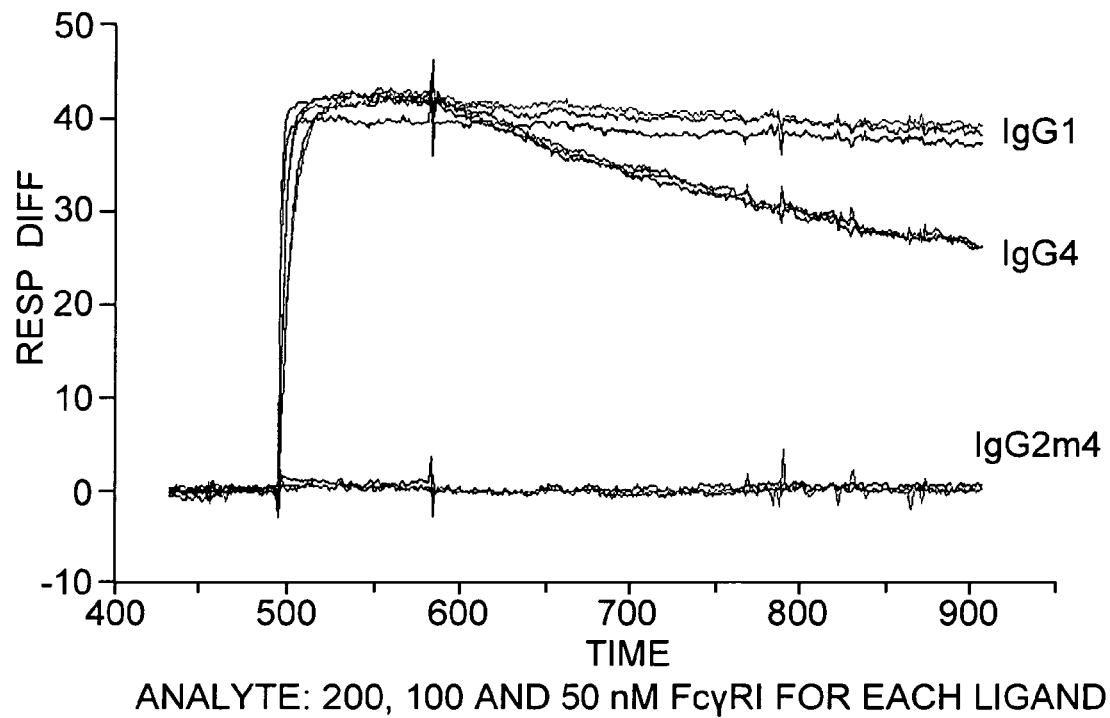
FIG. 2 shows the binding of an anti-ADDL IgG2m4 antibody to FcγRI (FIG. 2A), FcγRIIb/c (FIG. 2B), and the FcγRIII-LV polymorph (FIG. 2C) receptors as compared to the other isotypes indicated.

The invention disclosed herein is a modification of human IgG constant region structure which renders the IgG antibody incapable of provoking antibody-dependent cell-mediated cytotoxicity, binding to an Fc gamma receptor and complement-mediated cytotoxicity. Advantageously, an antibody containing this non-immunostimulatory IgG constant region does not exhibit a substantial modification of the binding to FcRn or half-life modification. Accordingly, the non-immunostimulatory IgG constant region of this invention is useful for producing any therapeutic antibody for which primary blocking activity and long pharmacokinetics are desired without any additional effector functionality.

While antibodies are exemplified herein, the present invention encompasses any antibody-like polypeptide which contains an Fc region. For example, the present invention also embraces immunoadhesins. As is well-known in the art, immunoadhesin are antibody-like molecules which combine the "binding domain" of a heterologous "adhesion" protein (e.g. a receptor, ligand or enzyme) with an immunoglobulin constant domain.

Antibody-dependent cell-mediated cytotoxicity, or ADCC, refers to a cell-mediated reaction in which nonspecific cytotoxic cells that express Fc receptors (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. Fc receptor expression on hematopoietic cells is summarized in Table 3 on page 464 of Ravetch and Kinet ((1991) *Annu. Rev. Immunol.* 9:457-92).

An antibody which lacks binding to an Fc gamma receptor is one which has either reduced or diminished Fc receptor binding activity and/or ADCC activity compared to a parent IgG antibody or to a polypeptide containing a native sequence Fc region. Such an antibody or polypeptide which displays reduced binding to an Fc receptor possesses little or no appreciable binding to an Fc receptor, e.g., 0-20% binding to the Fc receptor compared to a native IgG Fc region, e.g., as determined in the Examples herein. When used herein, a "native sequence" refers to an amino acid sequence identical to the amino acid sequence found in nature, including allotypes.

The terms "Fc receptor" or "FcR" are used to describe a receptor that binds to the Fc region of an antibody. The preferred FcR is a native human FcR. Moreover, a preferred FcR is one which binds an IgG antibody (a gamma receptor) and includes receptors of the FcγRI, FcγRII, and FcγIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see Daeron (1997) Annu. Rev. Immunol. 15:203-234). FcRs are reviewed in Ravetch and Kinet (1991) Annu. Rev. Immunol. 9:457-92; and de Haas, et al. (1995) J. Lab. Clin. Med. 126:330-41. Other FcRs, including those to be identified in the future, are encompassed by the term "FcR" herein. The term FcR as used herein is distinct from that of FcRn, which refers to the neonatal receptor, which is responsible for the transfer of maternal IgGs to the fetus (Guyer, et al. (1976) J. Immunol. 117:587; Kim, et al. (1994) J. Immunol. 24:249).

In addition to being incapable of binding FcγRI, FcγRII, or FcγRIII, an isolated non-immunostimulatory antibody of the present invention is concomitantly incapable of binding to C1q. C1q, which mediates the complement-mediated cytotoxicity (CMC) pathway, is a polypeptide that includes a binding site for the Fc region of an immunoglobulin. C1q together with two serine proteases, C1r and C1s, forms the complex C1, the first component of the CMC pathway. In this regard, the antibody of the present invention does not activate the CMC pathway.

The antibody of this invention is said to be isolated when it is present in the substantial absence of other biological macromolecules of the same type. Thus, an "isolated antibody" refers to an antibody which is substantially free of other antibodies; however, the molecule may include some additional agents or moieties which do not deleteriously affect the basic characteristics of the antibody (e.g., binding specificity, neutralizing activity, etc.).

The IgG of the instant antibody can be any isotype including IgA, IgD, IgE, IgG or IgM, or a subclass thereof, e.g., IgG1, IgG2, IgG3, IgG4, IgA1 or IgA2. However, in one embodiment, the IgG is an IgG2 as this isotype possesses a superior half-life in experimental models (Zuckier, et al. (1994) Cancer Res. 58(17):3905-8) and in retrospective analysis of isotype half-life after IGIV treatment (Alyanakian, et al. (2003) Vox Sanguinis 84:188).

In particular embodiments, the invention embraces a substantial portion of the amino acid sequence of the Fc region of IgG2. As is conventional in the art, the term "Fc region" refers to a C-terminal region of an immunoglobulin heavy chain. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The Fc region of an immunoglobulin generally encompasses two constant domains, CH2 and CH3. For clarity, amino acid residues referred to herein are based upon the Kabat numbering system (Kabat, et al. (1991) supra), unless otherwise specified.

As used herein, "a substantial portion of an IgG2 Fc region" is intended to mean that 80% to 98% of the amino acid sequence of the Fc region is that of native IgG2. In particular embodiments, at least 90%, 91%, 92%, 93%, 94%, 95%, 96%, 97%, or 98% of the amino acid sequence of the Fc region is from the native IgG2 amino acid sequence. In a preferred embodiment, at least 95% of the amino acid sequence of the Fc region is from the native IgG2 amino acid sequence. In other embodiments, the remaining 4% to 20% of the amino acid sequence of the Fc region is from IgG4. In still other embodiments, at least 4%, 5%, 6%, 7%, 8%, 9%, or 10% of the amino acid sequence of the Fc region is from IgG4.

The elimination of antibody-dependent cell-mediated cytotoxicity, binding to an Fc gamma receptor and complement-mediated cytotoxicity, is achieved by substituting selected amino acid residues of IgG2 Fc region. In some embodiments, said substitutions are restricted to the CH2 domain of IgG2 Fc. The CH2 domain of a human IgG Fc region (also referred to as "Cγ2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been suggested that the carbohydrate may provide a substitute for the domain-domain pairing and help stabilize the CH2 domain (Burton (1985) Mol. Immunol. 22:161-206).

In other embodiments, substitutions in the IgG2 Fc region are in one or more amino acid residues of the B/C loop (amino acid residues 265 to 270), an FcRn binding domain, and the F/G loop (amino acid residues 327 to 332) of IgG2 Fc (See FIG. 1). As is well-known in the art, there are FcRn binding domains located between amino acid residues 252 and 257, amino acid residues 307 and 311, and amino acid residues 433 and 436. In some embodiments, at least one amino acid substitution of the instant IgG2 Fc region is carried out in the FcRn binding domain located between amino acid residues 307 to 311. In other embodiments, at least two amino acid residue substitutions are made in the FcRn binding domain located between amino acid residues 307 to 311. In particular embodiments, the IgG2 Fc region contains amino acid residue substitutions at amino acid residues 268, 309, 330 and 331.

As used herein, an amino acid substitution to the replacement of at least one existing amino acid residue in a predetermined amino acid sequence with another different "replacement" amino acid residue. The replacement residue or residues can be "naturally occurring amino acid residues" (i.e., encoded by the genetic code) such as alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). Substitution with one or more non-naturally occurring amino acid residues is also encompassed by the definition of an amino acid substitution herein. A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman, et al. ((1991) *Meth. Enzym.* 202:301-336). To generate such non-naturally occurring amino acid residues, the procedures of Noren, et al. ((1989) *Science* 244:182) and Ellman, et al. ((1991) supra) can be used. Briefly, these procedures involve chemically activating a suppressor tRNA with a non-naturally occurring amino acid residue followed by in vitro transcription and translation of the RNA.

To minimize the generation of neoepitopes, particular embodiments embrace substituting the amino acid residues of the IgG2 Fc region with the corresponding IgG4 amino acid residues (i.e., amino acid residues located at the same position in IgG4). An exemplary non-immunostimulatory IgG2 Fc region composed of a substantial portion of the native human IgG2 Fc region with selective incorporation of human IgG4 amino acid residues is set forth herein is IgG2m4 (SEQ ID NO:1). In IgG2m4, amino acid residues 268, 309, 330, and 331 of IgG2 Fc were substituted with the corresponding amino acid residues of the IgG4 Fc region (see FIG. 1). These substitutions were point mutations which included his->gln at amino acid residue 268 (i.e., residue 147 of SEQ ID NO:1), val->leu at amino acid residue 309 (i.e., residue 188 of SEQ ID NO:1), ala->ser at amino acid residue 330 (i.e., residue 209 of SEQ ID NO:1), and pro->ser at amino acid residue 331 (i.e., residue 210 of SEQ ID NO:1).

As can be appreciated by the skilled artisan, any conventional method for creating amino acid residue substitutions can be employed to generate the instant Fc region. Such methods include, but are not limited to, preparation by site-directed (or oligonucleotide-mediated) mutagenesis, PCR mutagenesis, and cassette mutagenesis of an earlier prepared DNA encoding the Fc region.

Alternative embodiments of the present invention embrace allotypes of IgG2. There are two major alleles in human IgG2 that result in amino acid differences, plus additional silent nucleotide changes. The two changes resulting in amino acid polymorphisms are identified as IGHG2*01 and IGHG2*02 (Hougs, et al. 2001) *Immunogenetics* 52:242-8), also known as G2mn⁻ and G2mn⁺, respectively, for their ability to be detected by murine monoclonal antibody SH-21. The IGHG2*01 and IGHG2*02 polymorphisms have the following positional changes: IGHG2*01, P189 and V397; IGHG2*02, T189 and M397. The IGHG2*02 allele is the most prevalent allele in Caucasian populations with a predominance of 40-75%, prevalence in Asian populations of 15-75%, but a very low prevalence in African populations. (Hougs, et al. 2001) supra). Additionally, the IGHG*02 allele was the predominant allele in a Danish population, with a total predominance of 55% (30% homozygous for T189/M397, 51% heterozygous, and 19% homozygous for P189/V397; Hougs, et al. 2001) supra). Additionally, a key allotype in IgG4 with respect to this invention is residue 309, which is a Leu residue in IgG1 and IgG3, a Val residue in IgG2, and either a Leu or Val residue in IgG4 (Kim, et al. (2001) *J. Mol. Evol.* 53: 1-9). Thus, additional IgG alleles are also embraced by this invention.

As indicated, the IgG Fc region of the present invention can be used in the production of any non-immunostimulatory antibody or antibody-like protein, including humanized and therapeutic antibodies, and used in a method for preventing binding of an antibody to an Fc receptor or complement. An antibody, as used in accordance with the instant invention includes, but is not be limited to, polyclonal or monoclonal antibodies, and chimeric, human (e.g. isolated from B cells), humanized, neutralizing, bispecific or single chain antibodies thereof. Methods for producing antibodies are well-known in the art. See, e.g., Kohler and Milstein ((1975) *Nature* 256: 495-497) and Harlow and Lane (Antibodies: A Laboratory Manual (Cold Spring Harbor Laboratory, New York (1988)). Antibodies of the present invention can also be produced by recombinant methods by splicing desired heavy and light chain variable regions to an IgG Fc region of the invention to obtain a molecule with appropriate antigen specificity and biological activity. Humanized antibodies are also embraced by the present invention. See Morrison, et al. (1984) *Proc. Natl. Acad. Sci.* 81, 6851-6855; Neuberger, et al. (1984) *Nature* 312:604-608; Takeda, et al. (1985) *Nature* 314:452-454; Queen, et al. (1989) *Proc. Natl. Acad. Sci. USA* 86:10029-10033; WO 90/07861. Human antibodies can also be obtained using phage-display methods. See, e.g., U.S. Pat. No. 6,797,492, WO 91/17271, WO 92/01047, WO 93/12227 and WO 91/10741. Human antibodies can be selected by competitive binding experiments, or otherwise, to have the same epitope specificity as a particular mouse antibody.

Antibodies of the present invention can have additional moieties attached thereto. For example, a microsphere or microparticle can be attached to the antibody or antibody fragment, as described in U.S. Pat. No. 4,493,825, the disclosure of which is incorporated herein by reference.

There is a plurality of uses for the human antibody IgG structure of this invention including combining the IgG structure with any of a variety of $V_H$ and $V_L$ sequences as a therapeutic antibody in which the desire is to block either a ligand or a receptor, without any potential immunocomplex formation, but with retention of normal antibody pharmacokinetics. In particular, the instant invention finds application toward cell-based targets, e.g., receptors, wherein blockage of the signaling function of the receptor is desired, but without the desire to provoke ADCC, complement fixation, or the formation of immune complexes. Additionally, this invention can be used as part of an Fc-fusion protein that will bind a soluble or cell-bound ligand to disrupt a biological interaction of that ligand with its target, but without unwarranted inflammatory reactions on the target.

In particular, the instant IgG Fc region finds application in the production of 5G1.1, ABX-CBL, ABX-IL8, ANTEGREN, Anti-CD18, anti-IL-4Rα, anti-Aβ, anti-TREM1, anti-ddk1, anti-IGF1R, anti-IL13Rα1, Anti-CD11a, Anti-VEGF, ANTOVA, BIRR-1, BTI-322, C225, CDP571, CDP571, CDP850, CORSEVIN M, D2E7, ERBITUX, HER-CEPTIN, HNK20, Hu23F2G, HUMIRA, IC14, ICM3, IDEC-114, IDEC-131, IDEC-151, IDEC-152, INFLIX-IMAB, LDP-01, LDP-02, Campath-1H, Lym-1, LYMPO-CIDE, MDX-33, MDX-CD4, MEDI-500, MEDI-507, MEDI-507, NRLu10, OKT4A, anti-CD3 OKT3, OSTAVIR, OVAREX, PANOREX 17-1A, PROTOVIR, ABCIXIMAB, RAPTIVA, REMICADE, REOPRO, rhuMab-E25, RIT-UXAN, SB-240563, SB-240683, SCH55700, SIMULECT, SMART a-CD3, SMART M195, SMART 1D10, VITAXIN, XOLAIR, ZENAPAX, anti-IGF1-R, anti-TrkA, anti-TrkB, anti-PC1 (anti-ENPP1), anti-PD-L1, anti-EPO-R, anti-TPO-R, or any anti-receptor antibody for use in the treatment of diseases and conditions including rheumatoid arthritis, nephritis, GvHD, allograft rejection, psoriasis, multiple sclerosis, cancer (e.g., colon, ovarian, breast), SLE, stroke, Crohn's disease, RSV, toxic shock, asthma/allergy, Ulcerative Colitis, CLL, NHL, autoimmune disorders, AML and the like. Similarly fusions between the instant Fc region and the exodomain of TREM1 or ectodomain of TREM2 are useful for the respective treatment of complex diseases such as sepsis and cancer, or neurodegenerative diseases (e.g., multiple sclerosis, Alzheimer's Disease or Parkinson's Disease).

Antibody or antibody-like molecules of the instant invention can be administered as a component of a pharmaceutical composition or medicament. Pharmaceutical compositions or medicaments generally contain the active therapeutic agent and a variety of other pharmaceutically acceptable components. See Remington: The Science and Practice of Pharmacy, Alfonso R. Gennaro, editor, 20th ed. Lippincott Williams & Wilkins: Philadelphia, Pa., 2000. The preferred form depends on the intended mode of administration and therapeutic application. Pharmaceutical compositions can contain, depending on the formulation desired, pharmaceutically-acceptable, non-toxic carriers or diluents, which are defined as vehicles commonly used to formulate pharmaceutical compositions for animal or human administration. Diluents are selected so as not to affect the biological activity of the combination. Examples of such diluents are distilled water, physiological phosphate-buffered saline, Ringer's solutions, dextrose solution, and Hank's solution.

Pharmaceutical compositions can also contain large, slowly metabolized macromolecules such as proteins, polysaccharides such as chitosan, polylactic acids, polyglycolic acids and copolymers (such as latex-functionalized SEPHAROSE™, agarose, cellulose, and the like), polymeric amino acids, amino acid copolymers, and lipid aggregates (such as oil droplets or liposomes).

Administration of a pharmaceutical composition or medicament of the invention can be carried out via a variety of routes including, but not limited to, oral, topical, pulmonary, rectal, subcutaneous, intradermal, intranasal, intracranial, intramuscular, intraocular, or intra-articular injection, and the like. The most typical route of administration is intravenous followed by subcutaneous, although other routes can be equally effective. Intramuscular injection can also be performed in the arm or leg muscles. In some methods, agents are injected directly into a particular tissue where deposits have accumulated, for example, intracranial injection. In some embodiments, an antibody or antibody-like molecule is administered as a sustained-release composition or device, such as a MEDIPAD™ device.

For parenteral administration, antibody or antibody-like molecules of the invention can be administered as injectable dosages of a solution or suspension of the substance in a physiologically acceptable diluent with a pharmaceutical carrier that can be a sterile liquid such as water, oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are suitable liquid carriers, particularly for injectable solutions. Antibodies can be administered in the form of a depot injection or implant preparation which can be formulated in such a manner as to permit a sustained-release of the active ingredient.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced delivery.

For suppositories, binders and carriers include, for example, polyalkylene glycols or triglycerides; such suppositories can be formed from mixtures containing the active ingredient in the range of 0.5% to 10%, or more desirably 1%-2%.

Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained-release formulations or powders and contain 10%-95% of active ingredient, or more suitably 25%-70%.

Topical application can result in transdermal or intradermal delivery. Topical administration can be facilitated by co-administration of the agent with cholera toxin or detoxified derivatives or subunits thereof or other similar bacterial toxins (see Glenn, et al. (1998) *Nature* 391:851). Co-administration can be achieved by using the components as a mixture or as linked molecules obtained by chemical crosslinking or expression as a fusion protein.

Alternatively, transdermal delivery can be achieved using a skin path or using transferosomes (Paul, et al. (1995) *Eur. J. Immunol.* 25:3521-24; Cevc, et al. (1998) *Biochem. Biophys. Acta* 1368:201-15).

The instant antibody is an improvement in the art as it provides significant advantages over a conventional IgG1, IgG2, or IgG4. For example, because the instant antibody fails to bind C1q as strongly as IgG2, the present antibody is unable to activate the complement cascade, similar to the properties of an IgG4 in that respect. Furthermore, this antibody does not bind any of the Fcγ receptors at physiologically relevant levels, in particular, FcγRI, which eliminates any undesired NK-cell or T-cell activation. As such the antibody does not mediate ADCC of any kind, and eliminates a potential alternative sink for the antibody in vivo. Moreover, the inventive antibody retains the half-life and basic structure of an IgG2 thereby providing an alternative to traditional native IgG2 antibodies.

The invention is described in greater detail by the following non-limiting examples.

EXAMPLE 1

Generation of IgG2m4 Antibodies

IgG2m4 antibody derivatives were prepared to decrease Fc receptor engagement, C1q binding, unwanted cytotoxicity or immunocomplex formation while maintaining both the long half-life and pharmacokinetic properties of a typical human antibody. The basic antibody structure of IgG2m4 is that of IgG2, which has been shown to possess a superior half-life in experimental models (Zuckier, et al. (1994) *Cancer Suppl.* 73:794-799). The structure of IgG2 was modified to eliminate C1q binding, through selective incorporation of IgG4 sequences, while maintaining the typical low level of FcγR binding (Canfield and Morrison (1991) *J. Exp. Med.* 173:1483-1491). This was achieved by using cross-over points wherein sequences of IgG2 and IgG4 were identical, thereby producing an antibody containing natural Fc sequences rather than any artificial mutational sequences.

The IgG2m4 form of the human antibody constant region was formed by selective incorporation of human IgG4 sequences into a standard human IgG2 constant region, as shown in FIG. 1. Conceptually, IgG2m4 resulted from a pair of chain-swaps within the CH2 domain as shown in FIG. 1. Four single mutations were made corresponding to sequences from IgG4. The Fc residues mutated in IgG2 included His268Gln, Val309Leu, Ala330Ser, and Pro331Ser, which minimized the potential for neoepitopes. The specific IgG4 amino acid residues placed into the IgG2 constant region are shown in Table 1, along with other alternatives from the basic structure.

TABLE 1

| Residue (Kabat numbering) | Residue in IgG2 | Residue in IgG4 | Residue in IgG2m4 | Alternative residue in IgG2m4 | Comment |
|---|---|---|---|---|---|
| 189 | Pro or Thr* | Pro | Thr | Pro | Key polymorphism of IgG2; Pro residue present in IGHG*01 allotype and Thr residue present in IGHG2*02 allotype[a,b]. |
| 268 | His | Gln | Gln | — | Change in the B/C loop known to be involved in FcγRII binding[c]. |
| 309 | Val | Leu or Val | Leu | Val | FcRn binding domain |
| 330 | Ala | Ser | Ser | — | Key residue for C1q binding[d]; also potentially involved in binding FcγRII and FcγRIII[e]. |
| 331 | Pro | Ser | Ser | — | Key residue for C1q binding[d,f] and FcγRI binding[g]; also potentially involved in binding FcγRII and FcγRIII[e]. |
| 397 | Met or Val* | Val | Met | Val | Val residue present in IGHG*01 allotype and Met residue present in IGHG2*02 allotype[a]. |

*Positions marked with an asterisk are subject to allelic variations.
[a]Hougs, et al. (2001) supra.
[b]WO 97/11971.
[c]Medgyesi, et al. (2004) supra.
[d]Tao, et al. (1991) supra.
[e]Armour, et al. (1999) supra; Armour et al. (2003) supra.
[f]Xu, et al. (1994) supra.
[g]Canfield and Morrison (1991) supra.

EXAMPLE 2

Anti-ADDL Antibody

Figure 2B:
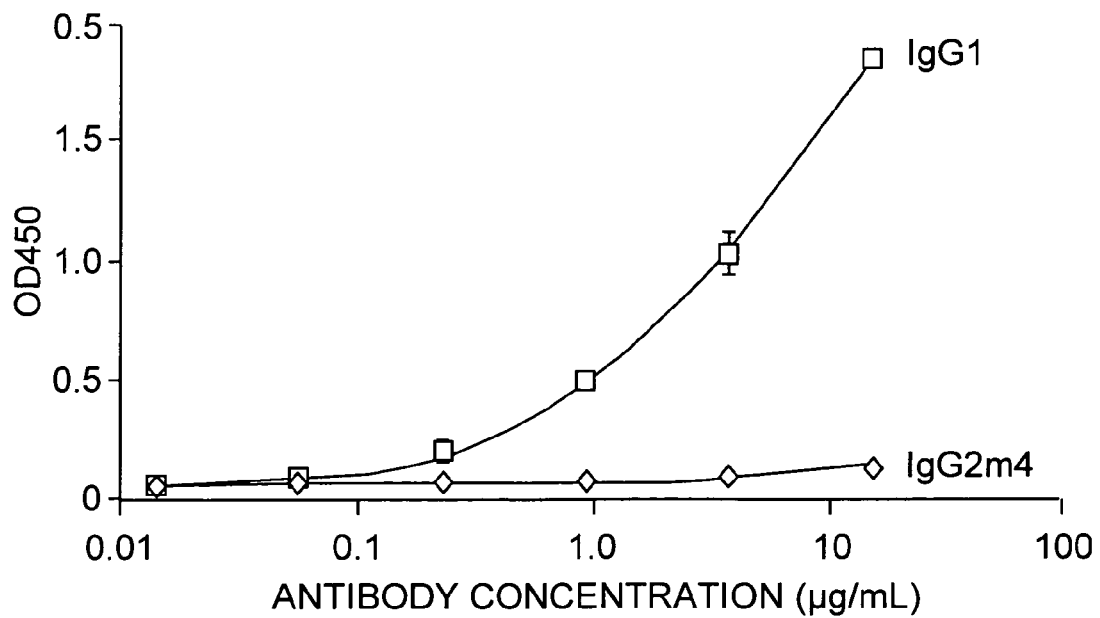
Figure 2C:
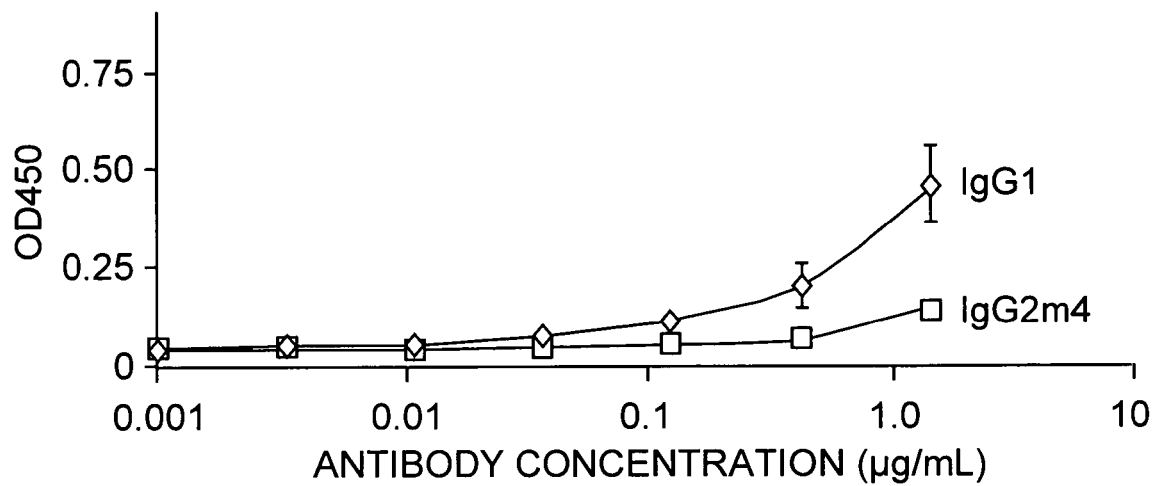
Figure 3:
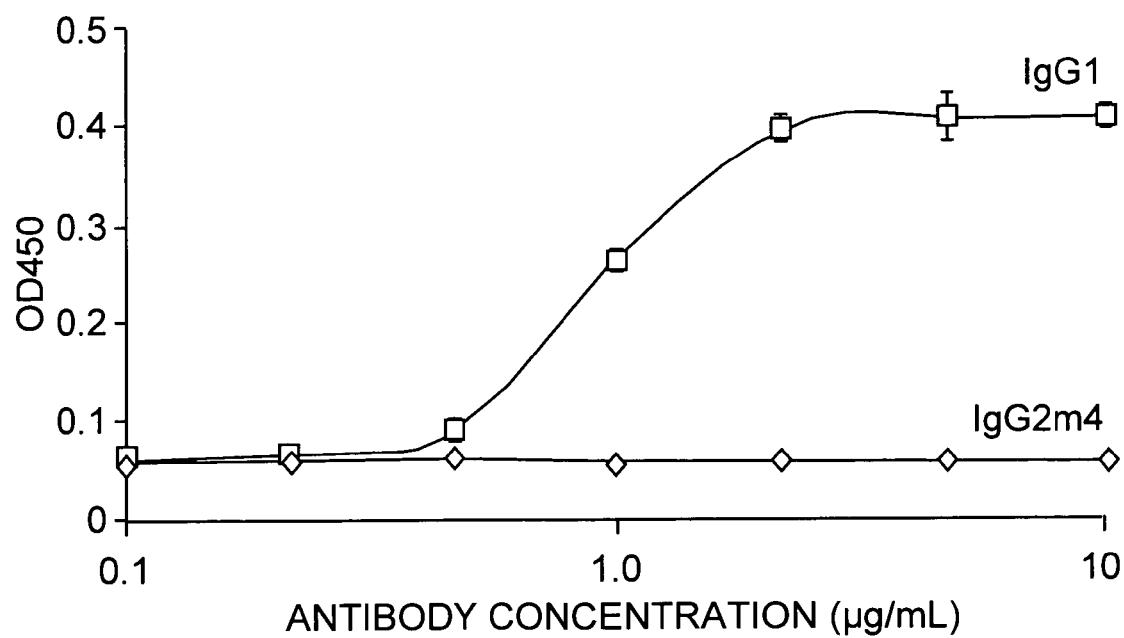
FIG. 3 shows a comparison of the binding of an IgG1 antibody and anti-ADDL IgG2m4 antibody to human complement (C1q).

To demonstrate the characteristics of the instant antibody, the $V_H$ and $V_L$ chains of an anti-Aβ-derived diffusible ligand (ADDL) antibody were fused to the IgG2m4 Fc region. The resulting anti-ADDL IgG2m4 antibody exhibited a mean serum clearance of $3.3 \times 10^{-3}$ mL/minute/kg and a terminal half-life of 12.6 days in nude mice and greater than 12 days in rhesus monkeys. Furthermore, under standard binding conditions and assays, the IgG2m4 constant region did not bind to human FcγRI, FcγRII, or FcγRIII receptors (see FIGS. 2A-2C, respectively) nor did it bind human C1q (FIG. 3).

---

What is claimed is:

1. An isolated non-immunostimulatory antibody comprising glutamine at residue 268, leucine at residue 309, serine at residue 330 and serine at residue 331 according to the Kabat numbering system,
    wherein the amino acid sequence of the Fc region of said antibody comprises at least 93% of the amino acid sequence of human immunoglobulin G2 (IgG2) Fc region, and
    wherein said antibody lacks antibody-dependent cell-mediated cytotoxicity, Fc gamma receptor binding and complement-mediated cytotoxicity.

2. The isolated non-immunostimulatory antibody of claim 1, wherein the amino acid sequence of the Fc region of said antibody is set forth in SEQ ID NO:1.

3. A pharmaceutical composition comprising the isolated non-immunostimulatory antibody of claim 1.

4. A kit comprising the isolated non-immunostimulatory antibody of claim 1.

* * * * *

SEQUENCE LISTING

<160> NUMBER OF SEQ ID NOS: 4

<210> SEQ ID NO 1
<211> LENGTH: 326
<212> TYPE: PRT
<213> ORGANISM: Artificial Sequence
<220> FEATURE:
<223> OTHER INFORMATION: Synthetic polypeptide

<400> SEQUENCE: 1

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Thr Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
            195                 200                 205

Ser Ser Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110
```

```
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 3
<211> LENGTH: 326
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Thr Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
                100                 105                 110
Pro Val Ala Gly Pro Ser Val Phe Leu Phe Pro Pro Lys Pro Lys Asp
            115                 120                 125
Thr Leu Met Ile Ser Arg Thr Pro Glu Val Thr Cys Val Val Val Asp
        130                 135                 140
Val Ser His Glu Asp Pro Glu Val Gln Phe Asn Trp Tyr Val Asp Gly
```

```
                145                 150                 155                 160
Val Glu Val His Asn Ala Lys Thr Lys Pro Arg Glu Glu Gln Phe Asn
                165                 170                 175

Ser Thr Phe Arg Val Val Ser Val Leu Thr Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 4
<211> LENGTH: 326
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Leu His Gln Asp Trp
            180                 185                 190
```

```
Leu Asn Gly Lys Glu Tyr Lys Cys Lys Val Ser Asn Lys Gly Leu Pro
        195             200             205
Ser Ser Ile Glu Lys Thr Ile Ser Lys Thr Lys Gly Gln Pro Arg Glu
    210             215             220
Pro Gln Val Tyr Thr Leu Pro Pro Ser Arg Glu Glu Met Thr Lys Asn
225             230             235             240
Gln Val Ser Leu Thr Cys Leu Val Lys Gly Phe Tyr Pro Ser Asp Ile
            245             250             255
Ala Val Glu Trp Glu Ser Asn Gly Gln Pro Glu Asn Asn Tyr Lys Thr
            260             265             270
Thr Pro Pro Met Leu Asp Ser Asp Gly Ser Phe Phe Leu Tyr Ser Lys
        275             280             285
Leu Thr Val Asp Lys Ser Arg Trp Gln Gln Gly Asn Val Phe Ser Cys
    290             295             300
Ser Val Met His Glu Ala Leu His Asn His Tyr Thr Gln Lys Ser Leu
305             310             315             320
Ser Leu Ser Pro Gly Lys
            325
```